United States Patent
Barve et al.

(10) Patent No.: US 7,820,859 B2
(45) Date of Patent: Oct. 26, 2010

(54) PROCESS FOR PREPARING L- (+) -LACTIC ACID

(75) Inventors: Prashant Purushottam Barve, Maharashtra (IN); Bhaskar Dattatreya Kulkarni, Maharashtra (IN); Sanjay Narayan Nene, Maharashtra (IN); Ravindra William Shinde, Maharashtra (IN); Milind Yashwant Gupte, Maharashtra (IN); Chandrashekhar Narayan Joshi, Maharashtra (IN); Gandhali Arun Thite, Maharashtra (IN); Vilas Bhiku Chavan, Maharashtra (IN); Tushar Ramchandra Deshpande, Maharashtra (IN)

(73) Assignee: Council of Scientific & Industrial Research, New Dehli (IN)

(*) Notice: Subject to any disclaimer, the term of this patent is extended or adjusted under 35 U.S.C. 154(b) by 0 days.

(21) Appl. No.: 11/996,246

(22) PCT Filed: Dec. 30, 2005

(86) PCT No.: PCT/IN2005/000455

§ 371 (c)(1),
(2), (4) Date: Dec. 1, 2008

(87) PCT Pub. No.: WO2007/010548

PCT Pub. Date: Jan. 25, 2007

(65) Prior Publication Data

US 2009/0203937 A1    Aug. 13, 2009

(30) Foreign Application Priority Data

Jul. 20, 2005  (IN)  .................. 1897/DEL2/005
Jul. 20, 2005  (IN)  .................. 1898/DEL/2005

(51) Int. Cl.
  *C07C 59/08*  (2006.01)
(52) U.S. Cl. ................................... 562/586
(58) Field of Classification Search ....................... None
  See application file for complete search history.

(56) References Cited

U.S. PATENT DOCUMENTS 2,290,926  A    7/1942   Weisberg et al.

(Continued)

OTHER PUBLICATIONS

A. Rodriguez, et al, "A Selective Method for the Preparation of Aliphatic Methyl Esters in the Presence of Aromatic Carboxylic Acids", Tetrahedron Letters, Elsevier, Amsterdam, NL, Nov. 19, 1998, pp. 8563-8566, XP004140582, vol. 39, No. 47.

*Primary Examiner*—Karl J Puttlitz
(74) *Attorney, Agent, or Firm*—Sughrue Mion, PLLC

(57) ABSTRACT

The present invention provides a commercially viable process for the preparation of highly pure and optically active L-(+)-lactic acid and S-(−)-methyl lactate, in high yield, obtained from esterification of aqueous crude lactic acid solution produced by sugar cane juice fermentation broth and methanol in continuous counter current trickle phase approach or in continuous counter current bubble column manner, using stabilizers and the methyl lactate so obtained is recovered and followed by purification of reasonably pure methyl lactate using reagent mixture such as sodium bi-carbonate, mono-ethanolamine or di-ethanolamine, urea or sodium-bicarbonate, mono-ethanolamine or di-ethanolamine, thiourea to reduce the impurity of dimethyl ester of dicarboxylic such as dimethyl oxalate or di-methyl succinate or methyl ester of mono-carboxylic acid such as methyl pyruvate present as an impurity, so as to get highly pure S-(−)-methyl lactate followed by hydrolyzing highly pure S-(−)-methyl lactate using highly pure lactic acid as a catalyst, using highly pure water as the hydrolysis media and by using pretreated activated carbon with dilute L-(+)-lactic acid, in batch or continuous mode. This very high pure S-(−)-methyl lactate constitutes an important product having interesting possibilities of application at an industrial level, in pharmaceuticals. Highly pure L-(+)-lactic acid thus obtained is used as an acidulant, as a food additive, for pharmaceutical applications, a monomer for making poly-lactic acid, as a monomer to prepare biodegradable polymer which are useful for manufacturing bags, application films, in the field of sanitary field, and has medical applications.

20 Claims, 2 Drawing Sheets

U.S. PATENT DOCUMENTS

Figure 1:
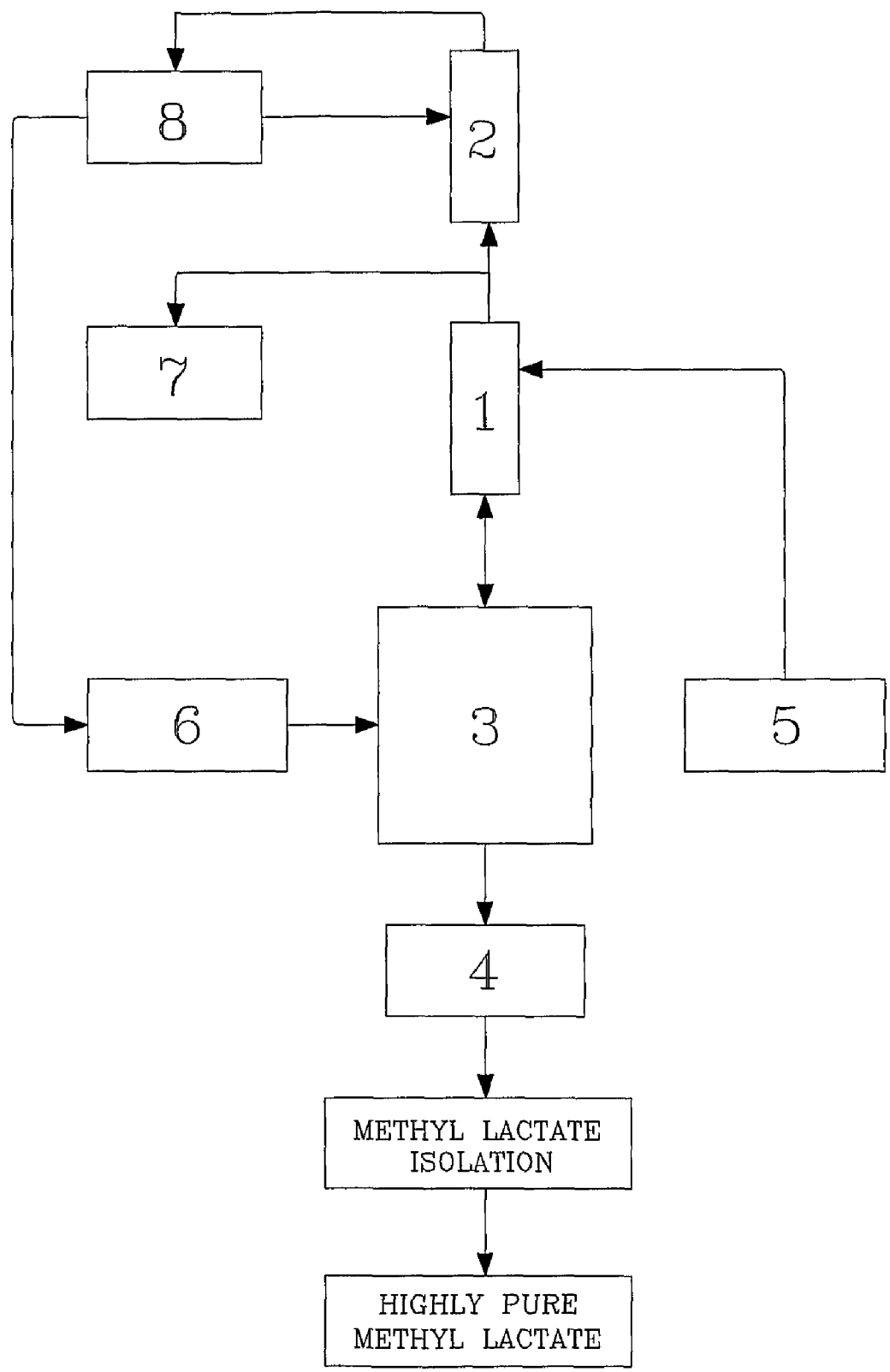

| | | | |
|---|---|---|---|
| 2,334,524 A * | 11/1943 | Wenker | 562/589 |
| 2,350,370 A * | 6/1944 | Schopmeyer et al. | 562/589 |
| 2,406,648 A | 8/1946 | Weisberg et al. | |
| 2,420,234 A * | 5/1947 | Filachione et al. | 560/179 |
| 5,210,296 A | 5/1993 | Cockrem et al. | |

* cited by examiner

FIGURE—1

PROCESS FOR PREPARING L-(+)-LACTIC ACID

CROSS REFERENCE TO RELATED APPLICATION

This application is a National Stage of International Application No. PCT/IN2005/000455 filed on Dec. 30, 2005, claiming priority based on Indian Patent Application Nos. 1897DEL2005 and 1898DEL2005, filed on Jul. 20, 2005, the contents of all which are incorporated herein by reference in their entirety.

FIELD OF THE INVENTION

The present invention relates to a process for the preparation of pure L-(+)-lactic acid from reasonably pure S-(−)-methyl lactate (~95-98% purity) obtained from calcium lactate, which is formed by sugar cane juice fermentation. More particularly the said process is related to the production of highly pure and optically active L-(+)-lactic acid in high yield, it relates particularly to a convenient and effective method for preparing L-(+)-lactic acid in high purity by hydrolyzing highly pure S-(−)-methyl lactate. Still more particularly it relates to continuous counter current trickle phase esterification of crude lactic acid using superheated methanol vapors with or without stabilizer and with optimum temperature, stream flow rates and pressure conditions. More particularly it is related to hydrolysis of calcium lactate obtained from sugar juice fermentation using dilute sulphuric acid in stoichiometric ratio followed by filtration to remove calcium sulphate and concentration of dilute lactic acid in evaporator to get desired concentrated crude lactic acid which is used as feed stock in continuous counter current trickle phase esterification. Still more particularly it relates to recovery of reasonably pure methyl lactate from continuous counter current trickle phase esterification section followed by purification using reagents followed by recovery to get highly pure S-(−)-methyl lactate which is subjected to hydrolysis using distilled, metal contamination free or de mineralized or de-ionized water, in the presence of highly pure L (+)-lactic acid as a catalyst to get highly pure L-(+)-lactic acid followed by activated carbon treatment where activated carbon is pre treated with dilute highly pure L-(+)-lactic acid solution in water to get highly pure L-(+)-lactic acid solution in water which may be concentrated in evaporator to desired strength.

BACKGROUND OF THE INVENTION

The high purity L-(+)-lactic acid has several industrial applications. The L-(+)-lactic acid so produced can be used in the production of dairy products, as an acidulating agent in the alimentary field, as an intermediate for the production of plasticizer agents, adhesives, pharmaceutical products, in the production of lactates, as a mordant in wool dying and so forth. Similarly, the high purity L-(+)-lactic acid prepared from a highly pure S-(−)-methyl lactate has considerable prospects of industrial development is in the field of production of biocompatible and biodegradable polymers which are useful for manufacturing bags, application films, in the field of sanitary field, medical applications and so on.

Purification of L-(+)-lactic acid; there are various manufacturing methods reported in the prior art namely, electro dialysis, extraction with base, adsorption and de-sorption, reactive distillation to prepare alkyl lactate followed by the hydrolysis of alkyl lactate to get lactic acid etc. This invention deals with the a process for the preparation of pure L-(+)-lactic acid from reasonably pure S-(−)-methyl lactate (~95-98% purity) obtained from calcium lactate which is formed by sugar cane juice fermentation. The manufacturing method for lactic acid is known from the prior art and in general, comprises three steps. In the step 1, alkali metal lactate is reacted with concentrated or dilute sulfuric acid. The corresponding alkali metal sulfate is produced as the side product along with the dilute aqueous solution of lactic acid. In the step 2, the dilute lactic acid solution is concentrated and esterified with methanol using a catalyst. In most of the invention the resultant mixture of methyl lactate, methanol and water is hydrolyzed with acidic catalyst to get lactic acid solution in water. Various methods of manufacturing lactic acid based on the above general method have been suggested in the past as cited in the following patented literatures:

Reference may be made to the U.S. Pat. No. 1,695,449, where in the manufacture of esters of lactic acid, which was done in a batch mode by boiling of 75% lactic acid solution with alcohol along with aluminum sulfate and removing the water of reaction by constant boiling mixture using benzene. Once the water of reaction is removed, the mixture is cooled and filtered to remove aluminum sulfate, neutralized to remove un-reacted lactic acid and ester then recovered by fractional distillation. The conversion of lactic acid reported in this run is 94.5 to 96.5%. However, the yield is not reported. This can be given as a typical example. The drawbacks of the of the above-mentioned prior art are, it can be seen that although the conversion of lactic acid is higher at 94.5%, the molar ratio of alcohol to the lactic acid is claimed to be greater than or equal to 8. Such use of excess of alcohol in the process leads to higher capital investment on recovery as well as higher operating cost of recovery at the industrial scale of manufacture. Further drawback is, this method requires the reaction to be carried out at constant boiling point mixture at 64.8° C.; at this temperature rate of conversion of lactic acid to its ester is not very high (Refer Ralph A. Tropue and Kenneth A. Kobe, Industrial Engineering Chemistry 42 (5), 801-810 (1950), Ralph A. Tropue and Kenneth A. Kobe, Ibid, 42 (7), 1403-1409 (1950)). The lower reaction temperature requires higher time to attain the desired conversion and directly affects the throughput and capital investment. Similarly in order to push the reaction to forward direction the water in the lactic acid and water of reaction has to be removed azeotropically with benzene. This requires distillation and recycles of benzene, many folds to the original water in the lactic acid and water of reaction. Similarly the distillate obtained may be in single phase or in two phases. Recovery of excess alcohol and benzene becomes a complicated operation, which also affects the process cost. Overall, this calls for larger reaction time and higher capital investment.

Reference may also be made to the U.S. Pat. No. 2,029, 694, wherein the method for manufacture of methyl lactate is described. Aqueous lactic acid is first dehydrated by heating to about 140° C., whereby the lactic acid gets converted to lactide and lactyl lactate. This is then reacted in a batch mode with small amount of methanol and sulfuric acid as the catalyst. Distillation of the reaction water, excess methanol and methyl lactate is carried out simultaneously at about 125° C. At the same time methanol is introduced in the reaction mixture held at 130 to 140° C., whereby the water of reaction, excess methanol and methyl lactate is distilled out in the co-current mode of the reactive distillation, from reaction mixture. The yield of methyl lactate based on lactic acid reported is around 83% and the mole ratio of methanol to lactic acid is around 3.0. The main drawback of this process is that it gives lower yield based on lactic acid despite using higher reaction temperature, which will affect the overall process economics. Further drawback is the higher reaction temperature promotes the polymerization of lactic acid and the formation of objectionable impurities like hydroxymethylfurfural or other undesired products. Some of these impurities are volatile in nature and distill along with methyl lactate. The distillate obtained by this process contains lot of water, methanol and methyl lactate and isolation of methyl lactate in pure form needs lot of additional energy. This is generally called as co-current approach of reactive distillation, where the product and bye-products are removed as the top product as a distillate, while the esterification is in progress. The product i.e. methyl lactate being higher boiler the temperature of the esterification still needs to be maintained at higher temperature to drive out the product and the bye product. While investigating this approach i.e. co-current approach for reactive distillation, we find 2-pentene-1-ol [1576-96-1] as the bye product and the impurity, along with hydroxymethylfurfural as reported in this patent i.e. U.S. Pat. No. 2,029,694. This was repeatedly observed in all the experiments where the distillation still temperature was 125° C. or more. It becomes very difficulty to remove this bye product 2-pentene-1-ol [1576-96-1] from methyl lactate. As per the available literature information, in the recovery cycle of methyl lactate, the side product 2-pentene-1-ol [1576-96-1] reacts with methyl lactate and trans-esterification occurs leaving away methanol as the bye product of the trans-esterification process. The bye product formed after trans-esterification of the methyl lactate i.e. bye product pentyl lactate is very difficult to hydrolyze to lactic acid, in the subsequent hydrolysis cycle of methyl lactate to recover pure lactic acid.

Reference further may be made to the U.S. Pat. No. 2,290,926 wherein the alkaline earth metal lactate preferably sodium lactate is heated along with the excess methanol and sulfuric acid at high temperature to get methyl lactate. This method has a drawback that it forms large amount of salt i.e. sodium sulfate which retains almost 35 to 40% of the methyl lactate in it as reported in the same invention. Further drawback is that in order to recover methyl lactate occluded in the sludge of sodium sulfate, water is added and the methyl lactate is removed by azeotropic distillation. The isolation of lactic acid by hydrolysis of methyl lactate obtained by this process suffers major purity problem such as the crude sodium lactate used for esterification contains lot of other carboxylic acid impurities like pyruvic acid, succinic acid, acetic acid etc, which are the bye product generated in the fermentation cycle. All these carboxylic acid impurities also get converted to their respective methyl esters and contaminate methyl lactate obtained by azeotropic distillation using water and contain the trace impurities of other carboxylic acid, which contaminates lactic acid recovered by hydrolyzing methyl lactate. Further drawback of this invention is that optical purity & quality of methyl lactate used & lactic acid obtained is not reported.

Reference further may be made to the U.S. Pat. No. 2,406,648, U.S. Pat. No. 2,390,140 and U.S. Pat. No. 2,434,300 wherein a mixture of alkaline earth metal lactate preferably sodium lactate, methanol and sulfuric acid is heated to get methyl lactate. During the esterification reaction in progress, the reaction mixture pH is maintained between 0.7 to 1.4 pH values. The main drawback of the invention is, the weight ratio of methanol to lactic acid salt (on 100% basis of alkali metal salt of lactic acid) is maintained from 3 to 6, this works out the mole ratio of methanol to lactic acid as 10.5 to 21 or even up to 52.5 of mole ratio. Use of such a high amount of methanol in esterifier has clear cut drawback and it increases loading on the recovery and recycle of methanol and commercially such operations are capital intensive and requires higher running cost. Further, this method has a drawback that it forms the large amount of salt i.e. sodium sulfate as the waste product, which retains lot of methyl lactate in it. In order to recover methyl lactate occluded in the sludge of sodium sulfate, the mixture is flash distilled under reduced pressure on mineral oil. The oil recovery and recycle in such operations on commercial level become difficult and messy. Further drawback is, to purify methyl lactate; water from methyl lactate is removed by azeotropic distillation. Commercially azeotropic distillation requires large amount of energy. The optical and chemical purity of methyl lactate produced is not mentioned in this invention.

Reference also may be made to the U.S. Pat. No. 2,334,524 and U.S. Pat. No. 2,350,370; wherein a method for manufacture of lactic acid from methyl lactate hydrolysis is reported, where the methyl lactate is derived from crude lactic acid. In this invention, relatively low excess of methanol is charged in to a still with 60% to 85% of crude lactic acid and a little mineral acid, such as sulfuric acid as the catalyst. The ester i.e. methyl lactate distills of along with water and methanol in a continuous co-current manner, the distilled methyl lactate is hydrolyzed with the help of catalyst, the generated lactic acid is taken out of the hydrolysis still as the product and methanol is recycled back to the esterification still. The main drawback of this invention is that, the crude lactic acid contains lot of other carboxylic acid such as acetic acid, succinic acid and pyruvic acid as the fermentation bye products, these acids also forms corresponding esters with methanol and gets steam distilled along with methyl lactate. If the methyl lactate is not further purified by fractional distillation, the carboxylic acids generated in hydrolysis cycle of methyl lactate, gets contaminated with acetic acid, succinic acid and pyruvic acid etc., all these carboxylic acids reduces the quality of lactic acid which is not addressed in this invention.

Reference also may be made to the U.S. Pat. No. 5,210,296, wherein methods for manufacture of butyl lactate from esterification of crude ammonium lactate, excess of butanol and sulfuric acid is described. The product butyl lactate is prepared in batch mode by treating ammonium lactate with sulfuric acid and butanol and purified by fractional distillation. The patent has reported about the impurities like acetic acid and succinic acid in the crude ammonium lactate, but has not reported about the chemical purity of butyl lactate. Similarly, the process has a drawback that, it uses ammonia, which is costly base compared to lime to neutralize the lactic acid in the fermentor and does not become commercially viable option. Further to it, the process has drawback that it produces waste ammonium sulfate, which contains lot of occluded butanol in it.

Reference also may be made to the U.S. Pat. No. 6,342,626 B1, wherein a method for manufacture of methyl lactate from 73% lactic acid in two stages (at high temperature 200° C. and high pressure of 20 kg/cm$^2$) is described. The process is carried out in two stages; first stage equilibrium conversion of lactic acid reported is about 80% and after isolating bye products of first stage, the second stage gives remaining conversion of lactic acid. The drawback of the process is that it is equilibrium-based process, involves high temperature and pressure. Further drawback is that, lactic acid being corrosive the cost of the commercial manufacturing setup will be very high. Further to it, the lactic acid is known to recemize at higher temperature (C. H. Holtan, Lactic Acid, properties and chemistry of lactic acid derivatives, Printer Oswald Schmidt KG Leipzig, 1971, page 149). The further drawback of the invention is that optical purity and the chemical purity of the methyl lactate produced is not reported.

The general method of preparation of lactic acid from crude lactic acid obtained from fermentation broth reported in the prior art is by the esterification of crude lactic acid by co-current method of reactive distillation where, the product methyl lactate, bye product water and excess methanol is taken out of reactive distillation still as a top product by maintaining the still at higher temperature. This leads to the accumulation of the acidity at the reactive distillation still and give rise to the objectionable bye-products like hydroxyl methyl furfural, 2-pentene-1-ol etc. Further as per the reported methods in the prior art, in this method of reactive distillation methyl lactate distills out along with excess methanol, the water and along with methyl esters of other carboxylic acids formed as bye product in fermentation and this mixture is further hydrolyzed without purification of methyl lactate. The purity of methyl lactate will thus govern the purity of lactic acid produced. In the prior art reported, most of the inventions do not report the impurity profile of the methyl lactate and lactic acid and its optical purity.

In the present invention, the method of preparation of methyl lactate from crude lactic acid is a continuous counter current trickle phase esterification of crude lactic acid where, the product methyl lactate is removed continuously from the reactive distillation still bottom, whereas the excess methanol, water associated with crude lactic acid and the bye product water are removed from the column top continuously. Since water is being separated from the product i.e. methyl lactate the operation mode gives higher conversion of lactic acid. Similarly this mode of operation does not allow building of excess acidity at reactive distillation still. Since the water associated with crude lactic acid and water of reaction is removed continuously by excess alcohol, the rate of formation of methyl lactate is very high; therefore there is no need to maintain the still at higher temperature to achieve complete conversion of lactic acid. Since the reaction is carried out at moderate condition so as to avoid formation of any bye-products, impurities such as hydroxymethylfurfural and 2-pentene-1-ol etc., the method of the present invention can be conveniently operated at commercial scale, Similarly, by appropriate designing, the countercurrent trickle phase mass transfer (column) approach reported in the present invention, the desired throughput as well as the complete conversion of lactic acid to methyl lactate could be achieved.

Further the method of conversion of reasonably pure methyl lactate to highly pure methyl lactate is also demonstrated. Further it is demonstrated that, the hydrolysis of highly pure methyl lactate leads to highly pure lactic acid. The method of preparation of highly pure methyl lactate from reasonably pure methyl lactate involves the use of chemical treatment of reasonably pure methyl lactate with various reagents. The reasonably pure methyl lactate contains various carboxylic acid methyl esters as the bye products formed in the fermentation cycle such as dimethyl-oxalate, dimethyl-succinate, methyl acetate, methyl pyruvate etc. Before hydrolysis of such an impure methyl lactate with water, it is first treated with sodium bicarbonate, mono-ethanolamine [141-43-5] or di-ethanolamine [11-42-2], urea or sodium-bicarbonate, mono-ethanolamine or di-ethanolamine, thiourea mixture to convert these impurities to non volatile components and the methyl lactate is isolated by distillation as highly pure S-(−)-methyl lactate which is then subjected to hydrolysis to L-(+)-lactic acid in high purity. Since, there are no additional chemicals used during hydrolysis of the highly pure S-(−)-methyl lactate, the use of highly pure water and L-(+)-lactic acid as catalyst and pre-treated carbon, results in L-(+)-lactic acid of high purity. Pre-treatment of activated carbon, where pre-treatment of activated carbon is carried out by washing activated carbon with highly pure dilute lactic acid, this helps in removal of water soluble adhered impurities on the activated carbon as a result use of such pre-treated activated carbon gives highly pure lactic acid.

OBJECTIVES OF THE INVENTION

The main objective of the present invention is to provide a process for preparation of highly pure L-(+)-lactic acid and highly pure S-(−)-methyl lactate which obviates the drawbacks as detailed above.

This present invention provide a commercially viable process for the preparation of the alkyl ester of lactic acid, from aqueous solution of crude lactic acid obtained from the sugar cane juice fermentation process, using continuous counter-current trickle phase manner of reactive distillation and hydrolysis of highly pure methyl lactate thus obtained to highly pure L-(+)-lactic acid.

Another object of the present invention is to get very high pure S-(−)-methyl lactate which can be hydrolyzed with or without using catalyst to get high purity lactic acid. High purity lactic acid thus obtained is used as a monomer for making poly-lactic acid, as a monomer to prepare biodegradable polymer, as an acidulant, as a food additive and for pharmaceutical applications.

Yet another object of the present invention is that the process has particular application to the simultaneous esterification of free lactic acid in admixture with impurities of fermentation and even in the presence of water.

Yet another object of the present invention is to use moderate mole ratio of methanol to lactic acid during counter current trickle phase esterification.

Yet another object of the present invention is to get high conversion during counter current trickle phase esterification by using super heated methanol vapors and optimum temperature, flow rates, pressure conditions during operation.

Still another object of the present invention is that the process be carried out at moderate temperature with very high conversion of dilute lactic acid to methyl lactate.

Yet another object of the present invention is to prepare very high purity S-(−)-methyl lactate in a continuous manner from dilute crude lactic acid and by recycling un-reacted methanol there by making process commercially viable.

Yet another objective of this present invention is to avoid the polymerization and oxidation of the lactic acid to pyruvic acid by incorporating the stabilizers in the reaction zone.

Another object is to provide purification of reasonably pure methyl lactate to highly pure S-(−)-methyl lactate using reagents.

Yet another object is to provide a process for the purification and hydrolysis of S-(−)-methyl lactate to free L-(+)-lactic acid.

Yet another object of the present invention is to provide a process that could be carried out at moderate temperature and high conversion of S-(−)-methyl lactate to L-(+)-lactic acid.

Yet another object is to prepare very high purity L-(+)-lactic acid from reasonably pure methyl lactate by treating the methyl lactate with sodium bicarbonate, mono-ethanolamine or di-ethanolamine, urea or sodium-bicarbonate, mono-ethanolamine or di-ethanolamine, thiourea mixture.

Yet another object of the present invention is to prepare very high purity L-(+)-lactic acid from pure or reasonably pure methyl lactate and by recycling methanol obtained from hydrolysis reaction to the esterification section, there-by making process commercially viable.

Still another object of the present invention is to get L-(+)-lactic acid in very high purity as a odor free L-(+)-lactic acid and is use as a monomer for making polylactic acid, as a monomer to prepare biodegradable polymer, as an acidulant, as a food additive and for pharmaceutical applications.

Figure 2:
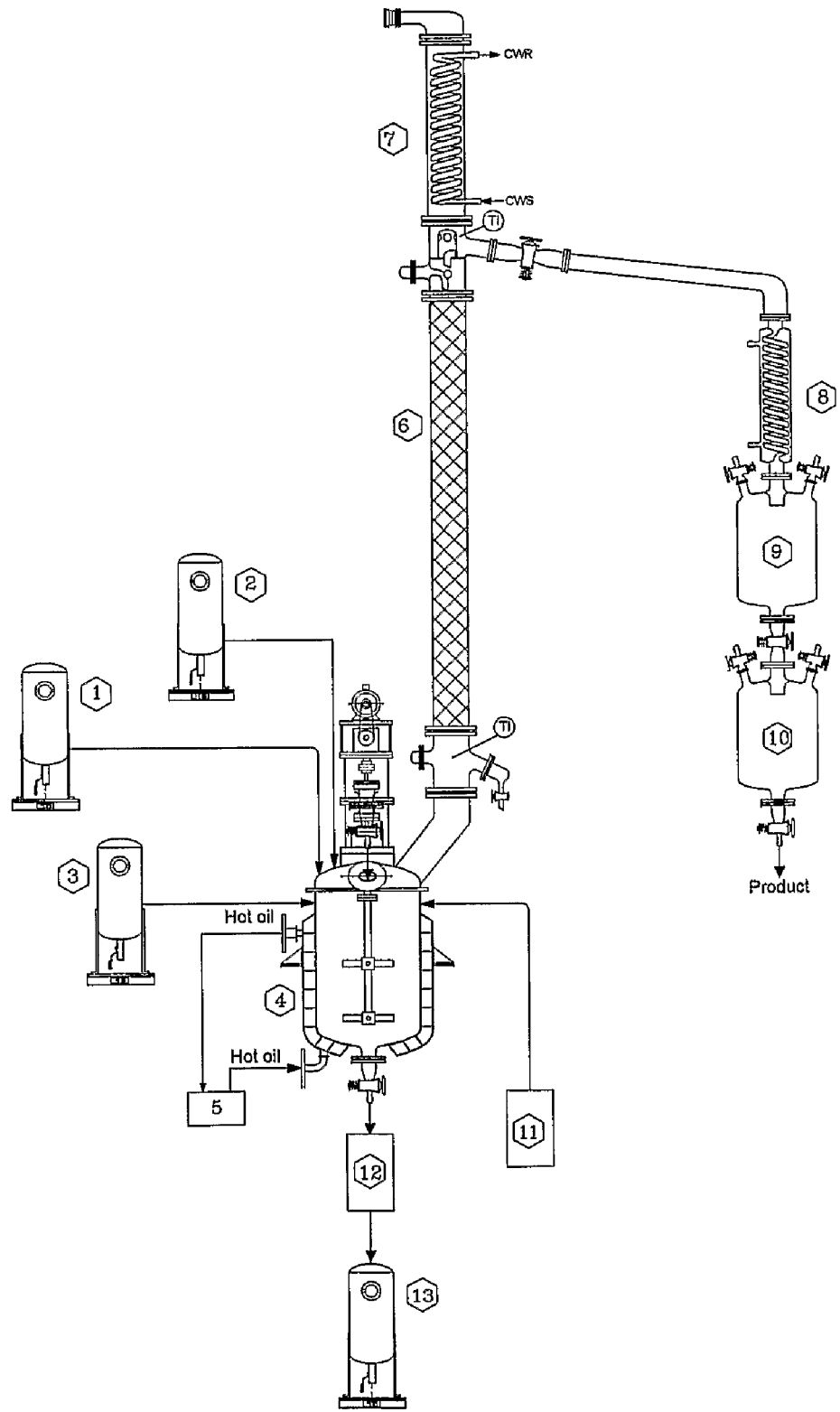

In the drawings accompanying this specification,

FIGS. 1 and 2 represents the setup of this present invention mentioned.

STATEMENT OF THE INVENTION

Accordingly the present invention provides a process for preparation of highly pure L-(+)-Lactic acid, the said process comprising the steps of:

(a) esterifying crude dilute lactic acid solution in water using mineral acid by preheating the above said crude dilute lactic acid at a temperature of about 105° C. and allowing it to react with superheated methanol vapors maintained at about 150° C. in desire stoichiometric ratio, optionally in the presence of stabilizer, in continuous counter current trickle phase mode to obtain the methyl lactate, removing continuously un reacted methanol and water rich layer separately as distillate and crude methyl lactate in a continuous manner as overflow from reactor bottoms followed by recovery of reasonably pure methyl lactate using evaporator with lactic acid to methyl lactate conversion of about 98.5% with no other bye product formation, (b) reacting the above said reasonably pure methyl lactate having purity 93-95% by wt with reagent capable of being converting volatile components into non-volatile components, under reflux, for a period of 1 hr, followed by distillation with or without vacuum to obtained desired highly pure S-(−)-methyl lactate having purity of 99.8% by wt, moisture of 0.03% and optical purity of (−) 8.43°, (c) hydrolyzing the above said highly pure S-(−)-methyl lactate obtained in step (b) with distilled, metal contamination free or de mineralized or de-ionized water, in the presence of highly pure L(+)-lactic acid as catalyst with a molar ratio of S-(−)-methyl lactate to catalyst in the range of 10.8:1 to 3.4:1, at a temperature in the range of 85-105° C., for a period of 2-6 hrs and allowing hydrolysation of S-(−)-methyl lactate to L-(+)-lactic acid with the removal of methanol obtained during hydrolysis reaction continuously under reflux, at controlled temperature and pressure to obtain the highly pure L-(+)-lactic acid followed by treating with pretreated activated carbon to obtain the highly pure L-(+)-lactic acid solution in water and concentrating it in an evaporator to desired strength having purity in the range of 99-99.8% and optical purity of 99-99.9% on water free basis without any bye product and continuously collecting the methanol in a reservoir for being used/recycled in step (a).

In an embodiment of the present invention the said process is characterized in step (b) in converting volatile impurities of S-(−)-methyl lactate into non volatile components before hydrolysis by using a mixture of sodium bicarbonate with a reagent selected from the group consisting of urea, mono ethanolamine, di-ethanolamine and a mixture thereof.

In yet another embodiment the said process is characterized in step (c) in using pure lactic acid as catalyst for accelerating the hydrolysis of S-(−)-methyl lactate.

In yet another embodiment, the said process is characterized in step (a) in continuous counter current trickle phase esterification of heated lactic acid with super heated methanol in vapor phase in counter current mode and obtaining S-(−)-methyl lactate in a continuous mode.

In yet another embodiment, the said process is characterized in step (a) in using stabilizer selected from 4-methoxy phenol and hydroquinone.

In yet another embodiment the volatile impurity present in methyl lactate having purity of about 95% used in step (b) is mono or dicarboxylic acid ester selected from dimethyl oxalate, dimethyl fumarate, methyl acetate and a mixture thereof.

In yet another embodiment the catalyst used in step (c) is pure lactic acid having quality of about 90% by wt.

In yet another embodiment the activated carbon used in step (c) is pretreated by washing it with about 10% aqueous solution of pure L-(+)lactic acid.

In yet another embodiment, the said process is characterized in step (c), wherein the molar ratio of methyl lactate to catalyst, lactic acid, used is 4.8:1.0.

In yet another embodiment the time period used in step (c) for complete hydrolysis of methyl lactate is preferably in the range of 4-6 hrs.

In yet another embodiment the purity of lactic acid obtained in step (c) is about 99.8% by wt. on water free basis.

In yet another embodiment the optical purity of lactic acid obtained in step (c) is 99.9%.

In yet another embodiment the fresh or recycled methanol used for esterification of lactic acid in step (a) is a super heated methanol vapor.

In yet another embodiment wherein the use of stabilizer increased the lactic acid to methyl lactate conversion from 95% to 98.5% with no other bye product formation.

In yet another embodiment wherein the mole ratio of methanol to lactic acid 2.8:1 to 4:1, preferably 2.8 to 1.

In yet another embodiment the ratio of catalyst such as sulfuric acid to lactic acid is in the range of 0.005:100 to 0.02:100 on mole basis, preferably, 0.01:100 on mole basis.

In yet another embodiment the high purity of S(−)-methyl lactate obtained is in the range of 99.50 to 99.85% by wt. with about 0.03% by wt moisture.

In yet another embodiment, the said process is characterized in step (b) wherein the use of sodium bicarbonate is made in the fractionation of methyl lactate and is in the range of 1 to 5% by wt of methyl lactate, preferably 1% by wt of methyl lactate.

In still another embodiment the L-(+)-lactic acid produced is odor and color free.

DETAILED DESCRIPTION OF THE INVENTION

Accordingly, the present invention provides a process for the preparation of highly pure S-(−)-Methyl lactate, which comprises converting commercial grade calcium lactate obtained by fermentation of sugar cane juice or by fermentation of the starch, to crude lactic acid by acidification of calcium lactate with stoichiometric equivalent of sulfuric acid in having the strength from (10% to 98%, ?) to obtain dilute lactic acid solution in water, concentrating the dilute lactic acid optionally under reduced pressure using evaporator to obtain crude lactic acid in water having strength of 40% to 75%, esterifying crude lactic acid by methanol in presence of a catalyst and optionally in presence of a stabilizer to methyl lactate by the continuous counter current trickle phase or bubble column reactive distillation to obtain crude methyl lactate followed by recovery using evaporator under reduced pressure to get reasonably pure methyl lactate.

Further the present invention involved the purification of reasonably pure methyl lactate to highly pure S-(−)-methyl lactate followed by hydrolysis of a pure S-(−)-methyl lactate by highly pure water in presence of highly pure lactic acid as the catalyst for hydrolysis. The methanol being bye product of the process is driven out of the system continuously by distillation, which helps to drive the hydrolysis reaction in the forward direction and also helps in complete conversion of the S-(−)-methyl lactate to L-(+)-lactic acid. The resulting L-(+)-lactic acid solution obtained is decolorized using pre-treated activated carbon if necessary. The methyl lactate can also be impure and may contain small impurities of dicarboxylic acid dimethyl ester or monocarboxylic acid methyl ester. Before hydrolysis of such an impure methyl lactate with water, it is first treated with sodium bi-carbonate, mono-ethanolamine [141-43-5] or di-ethanolamine [11-42-2], urea or sodium-bicarbonate, mono-ethanolamine or di-ethanolamine, thiourea mixture to convert these impurities to non volatile components and the methyl lactate is isolated as highly pure S-(−)-methyl lactate which is then subjected to hydrolysis to L-(+)-lactic acid in high purity. Since, there are no additional chemicals used during hydrolysis of the highly pure S-(−)-methyl lactate, the use of highly pure water and L-(+)-lactic acid as catalyst and pre-treated carbon, results in L-(+)-lactic acid of high purity.

The following examples are given by way of illustration and should not be construed to limit the scope of present invention.

In the drawings accompanying this specification, FIGS. 1 and 2 represents the setup of this present invention mentioned.

Example-1

Preparation of Crude Lactic Acid Feed Stock

The glass lined stirred reactor having capacity of 20 L, was charged 10% by wt solution of calcium lactate in water, obtained from fermentation of sugar cane juice. Then to the calcium lactate solution in water, 50% by wt sulfuric acid in water Was charged in a stoichiometric ratio to release free lactic acid slowly within 1-hour maintaining temperature at 30° C. The reaction mixture after further stirring for 60 minutes was filtered on the centrifuge. The wet cake of calcium sulfate was washed with water to remove adhered acidity. The wet cake of calcium sulfate was dried at 110° C. to give white calcium sulfate. The filtrate and washing were concentrated on the falling film evaporator under vacuum to get crude lactic acid. The crude lactic acid so obtained was viscous, dark reddish brown liquid and had impurities of fermentation. It was treated with activated charcoal and filtered to get transparent and clear crude lactic acid in water having concentration of 60%. This dilute crude lactic acid was used in the subsequent Examples given below.

Example-2

Esterification Using Trickle Phase Continuous Counter Current Method

Referring drawings accompanying this specification, FIG. 1 represents the setup of this present invention mentioned.

Dilute crude lactic acid prepared as explained in Example-1 was pre-mixed with concentrated sulfuric acid (1 mole % of lactic acid) and stored in tank (5). Crude lactic acid feed was continuously pumped through pre-heater at 960 g/h. The temperature of pre-heater was maintained by hot oil circulator so as to maintain crude lactic acid feed temperature at 96° C. The heated crude lactic acid was fed continuously at slightly above the mid of trickle phase reactive distillation section (1) column fixed above the reboiler (3). Fresh methanol containing 0.4% water was stored in methanol feedstock tank (6). This methanol was continuously pumped through pre-heater at 720 g/h. The pre-heater temperature was maintained by hot oil circulator so as to get superheated methanol vapors at 82° C. The superheated methanol vapors were bubbled through sparger at the bottom of reboiler (3) containing pre-mixed crude lactic acid from Example-1 and fresh methanol in stoichiometric ratio. The reboiler (3) was maintained at 101° C. by hot oil circulator.

The heated lactic acid obtained from lactic acid pre-heater was allowed to trickle down continuously through packed column section (1) and was allowed to react continuously with the super heated methanol vapors obtained from methanol pre-heater through re-boiler (3) which rise through trickle phase column (1) and (2). The methyl lactate formed and unconverted crude lactic acid was allowed to trickle down continuously through trickle phase column section (1) to the re-boiler (3). The crude methyl lactate formed along with the impurities was allowed to built-up in the re-boiler (3), till 8000 g of crude methyl lactate was received in re-boiler (3). Hewlett-Packard GC, model 5890 Series-II, was used to analyze methyl lactate content in the overflow and methanol content in distillate. Concentration of methyl lactate in re-boiler (3) was 65.5% by wt. where as the moisture content in the crude methyl lactate measured by Automatic Karl-Fischer, Lab India made instrument was 3.0% by wt.

The bottom temperature of trickle phase column section (1), fixed just above re-boiler (3) was observed continuously at 82° C. The water from crude lactic acid, the reaction water, excess methanol and small amount of methyl lactate vapors were continuously passed through the packed column section (2) fixed above trickle phase column section (1) and the vapors condensed in condenser fixed at top of column section (2) and fractionated continuously. The vapor temperature at the top of column section (2) was maintained continuously at 65° C. (at boiling point of methanol at atmospheric pressure) and column section (2) bottom temperature was observed at 80° C. The water rich layer containing some traces of methyl lactate was continuously recovered at the bottom of column section (2) and collected in (7) through cooler, whereas the methanol rich fraction was collected continuously in (8) thorough cooler.

This crude methyl lactate stock was used in the subsequent Examples in reboiler (3) as steady state feed. The methyl lactate selectivity observed was 94.5% based on the lactic acid converted to methyl lactate.

Example-3

Esterification Using Trickle Phase Continuous Counter Current Method

Referring drawings accompanying this specification, FIG. 1 represents the setup of this present invention mentioned.

Crude lactic acid prepared as explained in Example-1 was pre-mixed with concentrated sulfuric acid (1 mole % of lactic acid) and stored in tank (5). This crude lactic acid mixture was continuously pumped through pre-heater at 960 g/h. The temperature of pre-heater was maintained by hot oil circulator so as to maintain crude lactic acid feed temperature at 107° C. The heated crude lactic acid was fed continuously at the mid of trickle phase column section (1), fixed just above re-boiler (3). Fresh methanol feedstock containing 0.4% water was stored in tank (6) This methanol was continuously pumped through pre-heater at 720 g/h. The pre-heater temperature was maintained continuously by hot oil circulator so as to get superheated methanol vapors at 155° C. The superheated methanol vapors were bubbled through sparger at the bottom of reboiler (3) containing crude methyl lactate steady state feed stock obtained from Example-2. The reboiler (3) was maintained continuously at 112° C. by hot oil circulator.

The heated lactic acid obtained from lactic acid pre-heater was allowed to trickle down continuously through packed column section (1) and was allowed to react continuously with the super heated methanol vapors obtained from methanol pre-heater through re-boiler (3) which rise through trickle phase column (1) and (2). The methyl lactate formed and unconverted crude lactic acid was allowed to trickle down continuously through trickle phase column section (1) to the re-boiler (3). The crude methyl lactate formed along with the impurities was removed continuously in the form of over-flow from reboiler (3) through cooler at a rate 900 g/h. Concentration of methyl lactate in overflow was 69.7% by wt. where as the moisture content measured by Karl-Fischer instrument was 1.0% by wt.

The bottom temperature of trickle phase column section (1), was obtained continuously at 91° C. The vapor temperature at the top of column (2) was maintained continuously at 65° C. and column (2) bottom temperature was observed at 81° C. The water rich layer containing some traces of methyl lactate was continuously recovered at the bottom of column (2) and collected in (7) through cooler, whereas the methanol rich fraction was collected continuously in (8) thorough cooler. The methyl lactate selectivity observed was 96% based on the lactic acid converted to methyl lactate.

Example-4

Esterification Using Trickle Phase Continuous Counter Current Method with 4-methoxy Phenol as Stabilizer Referring drawings accompanying this specification, FIG. 1 represents the setup of this present invention mentioned.

Crude lactic acid prepared as explained in Example-1 was pre-mixed with concentrated sulfuric acid (1 mole % of lactic acid) and to it 150 ppm of 4-methoxy phenol based on lactic acid was charged and stored in tank (5). This crude lactic acid mixture containing 4-methoxy phenol was continuously pumped through pre-heater at 960 g/h. The temperature of pre-heater was maintained by hot oil circulator so as to maintain crude lactic acid temperature at 96° C. The heated crude lactic acid was fed continuously at the mid of trickle phase column section (1), fixed just above re-boiler (3). Fresh methanol feedstock containing 0.4% water was stored in tank (6). This methanol was continuously pumped through pre-heater at 720 g/h. The pre-heater temperature was maintained by hot oil circulator so as to get superheated methanol vapors at 85° C. The superheated methanol vapors were bubbled through sparger at the bottom of reboiler (3) containing crude methyl lactate steady state feed stock obtained from Example-2. The reboiler (3) was continuously maintained at 103° C. by hot oil circulator.

The heated lactic acid obtained from lactic acid pre-heater was allowed to trickle down continuously through packed column section (1) and was allowed to react continuously with the super heated methanol vapors obtained from methanol pre-heater through re-boiler (3) which rise through trickle phase column (1) and (2). The methyl lactate formed and unconverted crude lactic acid was allowed to trickle down continuously through trickle phase column section (1) to the re-boiler (3).

The crude methyl lactate formed along with the impurities was removed continuously in the form of over-flow from reboiler (3) through cooler at a rate 850 g/h. Concentration of methyl lactate in overflow was 78.3% by wt. where as the moisture content measured by Karl-Fischer instrument was 3.0% by wt.

The bottom temperature of trickle phase column section (1) was observed continuously at 83° C. The vapor temperature at the top of column (2) was maintained continuously at 65° C. and column (2) bottom temperature was observed at 79° C. The water rich layer containing some traces of methyl lactate was continuously recovered at the bottom of (2) and collected in (7) through cooler, whereas the methanol rich fraction was collected continuously in (8) thorough cooler. The methyl lactate selectivity observed was 98.5% based on the lactic acid converted to methyl lactate.

Example-5

Esterification Using Trickle Phase Continuous Counter Current Method with Hydroquinone as Stabilizer Referring drawings accompanying this specification, FIG. 1 represents the setup of this present invention mentioned.

Crude lactic acid prepared as explained in Example-1 was pre-mixed with concentrated sulfuric acid (1 mole % of lactic acid) and to it 150 ppm of hydroquinone was charged and stored in tank (5). This crude lactic acid mixture containing hydroquinone was continuously pumped through pre-heater at 960 g/h. The temperature of pre-heater was maintained by hot oil circulator so as to maintain crude lactic acid temperature at 96° C. The heated crude lactic acid was fed continuously at the mid of trickle phase column section (1), fixed just above re-boiler (3). Fresh methanol feedstock containing 0.4% water was stored in tank (6). This methanol was continuously pumped through pre-heater at 720 g/h. The pre-heater temperature was maintained by hot oil circulator so as to get superheated methanol vapors at 85° C. The superheated methanol vapors were bubbled through sparger at the bottom of reboiler (3) containing crude methyl lactate steady state feed stock obtained from Example-2. The reboiler (3) was continuously maintained at 103° C. by hot oil circulator.

The heated lactic acid obtained from lactic acid pre-heater was allowed to trickle down continuously through packed column section (1) and was allowed to react continuously with the super heated methanol vapors obtained from methanol pre-heater through re-boiler (3) which rise through trickle phase column (1) and (2). The methyl lactate formed and unconverted crude lactic acid was allowed to trickle down continuously through trickle phase column section (1) to the re-boiler (3).

The crude methyl lactate formed along with the impurities was removed continuously in the form of over-flow from reboiler (3) through cooler at a rate 850 g/h. Concentration of methyl lactate in overflow was 78.3% by wt. where as the moisture content measured by Karl-Fischer instrument was 3.0% by wt.

The bottom temperature of trickle phase column section (1) was observed continuously at 83° C. The vapor temperature at the top of column (2) was maintained continuously at 65° C. and column (2) bottom temperature was observed at 79° C. The water rich layer containing some traces of methyl lactate was continuously recovered at the bottom of (2) and collected in (7) through cooler, whereas the methanol rich fraction was collected continuously in (8) thorough cooler.

The methyl lactate selectivity observed was 98.5% based on the lactic acid converted to methyl lactate.

Example-6

Control Example

Esterification Using Trickle Phase Continuous Counter Current Method with Doping of Known Impurities in Lactic Acid Feed Referring drawings accompanying this specification, FIG. 1 represents the setup of this present invention mentioned.

Crude lactic acid prepared as explained in Example-1 was pre-mixed with concentrated sulfuric acid (1 mole % of lactic acid) and to it different impurities were added, such as oxalic acid, malic acid, acetic acid and fumaric acid all put together by dissolving in small amount of methanol (1% each of the impurity by wt lactic acid was added) was charged and stored in tank (5). This crude lactic acid mixture containing known impurities was continuously pumped through pre-heater at 1000 g/h. The temperature of pre-heater was maintained by hot oil circulator so as to continuously maintain crude lactic acid temperature at 96° C. The heated crude lactic acid was fed continuously at the mid of trickle phase column section 1, fixed just above re-boiler (3). Fresh methanol feedstock containing 0.4% water was stored in tank (6). This methanol was continuously pumped through pre-heater at 750 g/h. The pre-heater temperature was maintained by hot oil circulator so as to get superheated methanol vapors at 154° C. The superheated methanol vapors were bubbled through sparger at the bottom of reboiler (3) containing crude methyl lactate steady state feed stock obtained from Example-2. The reboiler (3) was continuously maintained at 119° C. by hot oil circulator The heated lactic acid obtained from lactic acid pre-heater was allowed to trickle down continuously through packed column section (1) and was allowed to react continuously with the super heated methanol vapors obtained from methanol pre-heater through re-boiler (3) which rise through trickle phase column (1) and (2). The methyl lactate formed and unconverted crude lactic acid was allowed to trickle down continuously through trickle phase column section (1) to the re-boiler (3).

The crude methyl lactate formed along with the impurities was removed continuously in the form of over-flow from reboiler (3) through cooler at a rate 840 g/h. Concentration of methyl lactate in overflow was 74.4% by wt. where as the moisture content measured by Karl-Fischer instrument was 0.9% by wt.

The bottom temperature of trickle phase column section (1) was observed continuously at 103° C. The vapor temperature at the top of column 2 was maintained continuously at 65° C. and column (2) bottom temperature was observed continuously at 82° C. The water rich layer containing some traces of methyl lactate was continuously recovered at the bottom of (2) and collected in (7) through cooler, whereas the methanol rich fraction was collected continuously in (8) thorough cooler. The methyl lactate selectivity observed was 95% based on the lactic acid converted to methyl lactate.

Example-7

Control Example

Esterification Using Continuous Co-Counter Current Method

Referring drawings accompanying this specification, FIG. 1 represents the setup of this present invention mentioned.

Crude lactic acid prepared as explained in Example-1 was pre-mixed with concentrated sulfuric acid (1 mole % of lactic acid) and stored in tank (5). This crude lactic acid mixture was continuously pumped through pre-heater at 900 g/h. The temperature of pre-heater was maintained continuously by hot oil circulator so as to maintain crude lactic acid temperature at 105° C. The heated crude lactic acid was fed continuously at the mid of trickle phase column section (1). Fresh methanol feedstock containing 0.4% water was stored in tank (6). This methanol was continuously pumped through pre-heater at 750 g/h. The pre-heater temperature was maintained by hot oil circulator so as to get methanol vapors at 65° C. The methanol vapors were bubbled through sparger at the bottom of reboiler (3) containing 2000 g of liquid paraffin to provide media for heat transfer to the feed mixture. The reboiler (3) was maintained continuously at 150° C. by hot oil circulator.

Heated lactic acid obtained from pre-heater was allowed to trickle down continuously through packed column of trickle phase column section (1), and column (2), it was allowed to react continuously with the heated methanol vapors obtained from pre-heater which rise through columns of trickle phase column section (1), and column (2). The vapors of methyl lactate formed, vapors of excess methanol and water vapors were allowed to rise from reboiler (3) to columns of trickle phase column section (1) and column (2). Which was then collected as distillate without reflux in reservoir (8) through cooler. The vapor temperature at the top of column (2) was observed at 86° C. Concentration of methyl lactate in the distillate was 49% by wt as measured by GC. Where as the moisture content in distillate was measured by Karl-Fischer instrument showed 21.0% by wt. The distillate was having typical pungent smell and showed concentrations of 2-pentene-1-ol [1576-96-1], which was confirmed by Shimadzu made GC-MS Model-QP5000, GC-17A and by HPLC. The methyl lactate prepared by this example only, showed 2-pentene-1-ol [1576-96-1] as the impurity.

Example-8

Isolation of Highly Pure Methyl Lactate

Referring drawings accompanying this specification, FIG. 1 represents the setup of this present invention mentioned.

Crude methyl lactate obtained as overflow from reboiler (3), as mentioned under Example-3 was charged continuously to Evaporator (4), that was maintained continuously at 110° C. through hot oil circulator and was continuously maintained under vacuum at 100 mm of mercury. The vapors of methanol, water and methyl lactate generated from Evaporator, were condensed thorough cooler and stored to get semi finished methyl lactate in reboiler till desired amount was build. After collection of the desired amount of semi-finished methyl lactate in reboiler, 1% by wt. of methyl lactate sodium bicarbonate was added to the reboiler. After collecting desired amount of semi finished methyl lactate, the reboiler temperature was maintained continuously at 90° C. through hot oil circulator and was continuously maintained under vacuum at 40 mm of mercury. All the impurities were separated by fractional distillation using reflux through the cooler and all the different components were separated through cooler. Highly pure methyl lactate fraction collected showed the purity of 99.58% by wt on GC analysis and was having 0.03% by wt. moisture. The optical rotation of neat liquid methyl lactate was measured (−) 8.43 by Polarimeter.

Example-9

Isolation of Highly Pure Methyl Lactate

Referring drawings accompanying this specification, FIG. 1 represents the setup of this present invention mentioned.

Crude methyl lactate obtained as overflow from reboiler (3), as mentioned under Example-4 was charged continuously to Evaporator (4), that was maintained continuously at 110° C. through hot oil circulator and was continuously maintained under vacuum at 100 mm of mercury. The vapors of methanol, water and methyl lactate generated from Evaporator, were condensed thorough cooler and stored to get semi finished methyl lactate in reboiler till desired amount was build. After collection of the desired amount of semi-finished methyl lactate in reboiler, 1% by wt. of methyl lactate sodium bicarbonate was added to the reboiler. After collecting desired amount of semi finished methyl lactate, the reboiler temperature was maintained continuously at 90° C. through hot oil circulator and was continuously maintained under vacuum at 40 mm of mercury. All the impurities were separated by fractional distillation using reflux through the cooler and all the different components were separated through cooler. Highly pure methyl lactate fraction collected showed the purity of 99.58% by wt on GC analysis and was having 0.03% by wt. moisture. The optical rotation of neat liquid methyl lactate was measured (−) 8.43 by Polarimeter.

Example-10

Hydrolysis of Highly Pure S-(−)-methyl Lactate to Get Highly Pure L-(+)-lactic Acid Referring drawings accompanying this specification, FIG. 2 represents the setup of this present invention mentioned.

2500 g of highly pure S-(−)-methyl lactate from reservoir (1), having purity 99.81% by on GC analysis as methyl lactate, obtained by reactive distillation of lactic acid and methanol followed by fractional distillation to isolate pure methyl lactate, was charged to the glass lined stirred reactor (4), having capacity of 10 L and was further charged with 2500 g of distilled water (De-ionized, glass distilled) from reservoir (2), along with 500 g of Purac Inc, USA make pure lactic (90% by wt on HPLC analysis) from reservoir (3). Temperature of reboiler was maintained continuously at 100° C. by hot oil circulator (5). The methanol vapors formed during hydrolysis reaction were allowed to rise through column (6) and condensed in cooler (7) and fractionated with proper reflux so as to get top temperature at 65° C. The methanol formed was continuously collected in reservoir (10) through cooler (8). Any trace amount of methanol or unconverted methyl lactate was recovered and recycled. After collecting desired amount of methanol in reservoir (10) through cooler (8), 1000 g of distilled water from reservoir (2) was charged to reactor (4) so as to get complete conversion of methyl lactate in to L-(+)-lactic acid. The water was removed by distillation and was collected in reservoir (9) through cooler (8) so as to get lactic acid free from methanol and methyl lactate in trace amount. After removing desired amount of water, the lactic acid in the reactor (4) was treated with 0.5% by wt of total material with pre-treated activated charcoal from reservoir (11). Where pretreatment of activated charcoal was done by washing activated charcoal with 10% solution of pure L-(+)-lactic acid in water. The pure L-(+)-lactic acid and the pre-treated activated charcoal in reactor (4) was stirred for 30 minutes, cooled to room temperature and the contents of reactor (4) were filtered on Buchner filter (12), to get highly pure L-(+)-lactic acid as the filtrate which was stored in reservoir (13). This L-(+)-lactic acid filtrate from (13) was clear and transparent and was further concentrated at 80° C. and under vacuum of 100 mm Hg till 90% by w/w of L-(+)-lactic acid solution in water was obtained. This L-(+)-lactic acid was analyzed by HPLC and showed lactic acid of 99.81% purity by wt. on water free basis and having optical purity of 99.9% as analyzed by RANDOX Enzyme Kit method. The L-(+)-lactic acid obtained was also free from any odor and color.

Hydrolysis reaction progress was analyzed by monitoring concentration of Methyl lactate in reactor. Hydrolysis reaction completed in 6 hrs as no traces of methanol or methyl lactate was observed in the same sample.

Data obtained by GC analysis is given below.

| Sr. No | Time (hrs) | Methyl lactate (%) w/w |
|--------|------------|------------------------|
| 1      | 0          | 92.81                  |
| 2      | 1          | 78.74                  |
| 3      | 2          | 45.09                  |
| 4      | 3          | 20.12                  |
| 5      | 4          | 10.60                  |
| 6      | 6          | Negligible             |

Example-11

Purification of Reasonably Pure Methyl Lactate to Pure S-(−)-methyl Lactate Using Urea Followed by Hydrolysis to Get Highly Pure L-(+)-lactic Acid Referring drawings accompanying this specification, FIG. 2 represents the setup of this present invention mentioned.

Reasonably pure methyl lactate 5000 g having purity 95.86% by GC analysis as methyl lactate was charged to the glass lined stirred reactor (4), having capacity of 10 L, and 50 g of sodium bi-carbonate and 50 g urea mixture was charged to the reactor; the reaction charge was refluxed for one hour at 80° C. and at 50 mm Hg pressure; then the methyl lactate was recovered under same vacuum and under reflux. Pure S-(−)-methyl lactate recovery was observed more than 98%. The highly pure S-(−)-methyl lactate recovered from above experiment (placed in the reservoir (1), having purity 99.79% by GC analysis as methyl lactate) was charged to the glass lined stirred reactor (4), having capacity of 10 L. The hydrolysis reaction of highly pure S-(−)-methyl lactate to highly pure L-(+)-lactic acid was followed exactly as mentioned under Example-10. The L-(+)-lactic acid obtained here was clear, transparent and odorless and was analyzed by HPLC and showed highly pure L-(+)-lactic acid of 99.80% purity by wt. on water free basis and having optical purity of 99.9% as analyzed by RANDOX Enzyme Kit method. No trace of methanol and methyl lactate was observed in the L-(+)-Lactic Acid as analyzed by GC. This L-(+)-lactic acid obtained was free from any odor. The complete conversion of S-(−)-methyl lactate into L-(+)-lactic acid was observed.

Example-12

Purification of Reasonably Pure Methyl Lactate to Pure S-(−)-Methyl Lactate Using Mono-Ethanolamine Followed by Hydrolysis to Get Highly Pure L-(+)-Lactic Acid

Referring drawings accompanying this specification, FIG. 2 represents the setup of this present invention mentioned.

Reasonably pure methyl lactate 5000 g having purity 94.43% by GC analysis as methyl lactate was charged to the glass lined stirred reactor (4), having capacity of 10 L, 50 g sodium bi-carbonate and 50 g of mono-ethanolamine mixture was charged to the reactor; the reaction charge was refluxed for one hour at 80° C. and at 50 mm Hg pressure; then the methyl lactate was recovered using same vacuum pressure and under reflux. The highly pure S-(−)-methyl lactate recovered from above experiment (placed in the reservoir (1), having purity 99.39% by GC analysis as methyl lactate) was charged to the glass lined stirred reactor (4), having capacity of 10 L. The hydrolysis reaction of highly pure S-(−)-methyl lactate to highly pure L-(+)-lactic acid was followed exactly as mentioned under Example-10. The L-(+)-lactic acid obtained here was clear, transparent and odorless and was analyzed by HPLC and showed highly pure L-(+)-lactic acid of 99.8% purity by wt. on water free basis and having optical purity of 99.9% as analyzed by RANDOX Enzyme Kit method. No trace of methanol and methyl lactate was observed in the L-(+)-Lactic Acid as analyzed by GC. This L-(+)-lactic acid obtained was free from any odor.

Example-13

Purification of Reasonably Pure Methyl Lactate to Pure S-(−)-Methyl Lactate Using Di-Ethanolamine Followed by Hydrolysis to Get Highly Pure L-(+)-Lactic Acid

Referring drawings accompanying this specification, FIG. 2 represents the setup of this present invention mentioned.

Reasonably pure methyl lactate 5000 g having purity 94.43% by GC analysis as methyl lactate was charged to the glass lined stirred reactor (4), having capacity of 10 L, 50 g sodium bicarbonate and 50 g of di-ethanolamine mixture was charged to the reactor; the reaction charge was refluxed for one hour at 80° C. and at 50 mm Hg pressure; then the methyl lactate was recovered using same vacuum pressure and under reflux. The highly pure S-(−)-methyl lactate recovered from above experiment placed in the reservoir (1), having purity 99.56% by GC analysis as methyl lactate) was charged to the glass lined stirred reactor (4), having capacity of 10 L. The hydrolysis reaction of highly pure S-(−)-methyl lactate to highly pure L-(+)-lactic acid was followed exactly as mentioned under Example-10. The L-(+)-lactic acid obtained here was clear, transparent and odorless and was analyzed by HPLC and showed highly pure L-(+)-lactic acid of 99.8% purity by wt. on water free basis and having optical purity of 99.9% as analyzed by RANDOX Enzyme Kit method. No trace of methanol and methyl lactate was observed in the L-(+)-lactic acid as analyzed by GC. This L-(+)-lactic acid obtained was free from any odor.

Example-14

Conversion of Impure Methyl Lactate to Highly Pure S-(−)-Methyl Lactate and Hydrolysis of Highly Pure S-(−)-Methyl Lactate to Get Highly Pure L-(+)-Lactic Acid

Referring drawings accompanying this specification, FIG. 2 represents the setup of this present invention mentioned.

Known 3000 ppm dicarboxylic acid and mono carboxylic acid esters impurities (like dimethyl oxalate, dimethyl fumarate, methyl acetate) were doped in reasonably pure methyl lactate 5000 g having purity 95.5% by GC analysis as methyl lactate, was charged to the glass lined stirred reactor (4), having capacity of 10 L, and 50 g of sodium bi-carbonate, 50 g urea and 50 g mono-ethanolamine mixture was charged to the reactor; the reaction charge was refluxed for one hour at 80° C. and at 50 mm Hg pressure; then the methyl lactate was recovered using same vacuum pressure and under reflux. The highly pure methyl lactate recovered from above experiment placed in the reservoir (1), having purity 99.78% by GC analysis as methyl lactate) was charged to the glass lined stirred reactor (4), having capacity of 10 L. The hydrolysis reaction of highly pure S-(−)-methyl lactate to highly pure L-(+)-lactic acid was followed exactly as mentioned under Example-10. The highly pure L-(+)-lactic acid obtained here was clear and transparent and was analyzed by HPLC and showed highly pure L-(+)-lactic acid of 99.79% purity by wt. on water free basis and having optical purity of 99.2% as analyzed by RANDOX Enzyme Kit method. No trace of methanol and methyl lactate was observed in the L-(+)-Lactic Acid as analyzed by GC. This L-(+)-lactic acid obtained was free from any odor.

Example-15

Conversion of Commercially Available Methyl Lactate to Highly Pure Methyl Lactate and Hydrolysis of Highly Pure Methyl Lactate to Get Highly Pure Lactic Acid

Referring drawings accompanying this specification, FIG. 2 represents the setup of this present invention mentioned.

2000 g Commercially available methyl lactate having purity 95.77% by wt. methyl lactate and 3.64% by wt methyl pyruvate as impurity analyzed on GC, and GC-MS, was charged to the glass lined stirred reactor (4), having capacity of 10 L, mono-ethanolamine was charged to the reactor as 2% of molar composition of methyl pyruvate present in feed methyl lactate, the reaction charge was refluxed for one hour at 80° C. and at 50 mm Hg pressure; then the methyl lactate was recovered using same vacuum and under reflux. Negligible traces of methyl pyruvate were seen in methyl lactate recovered as analyzed by GC-MS, thus making methyl lactate almost free form methyl pyruvate impurity. The highly pure methyl lactate recovered from above experiment placed in the reservoir (1), having purity 99.8% by wt. methyl lactate GC analysis as methyl lactate) was charged to glass lined stirred reactor (4), having capacity of 10 L. The hydrolysis reaction of highly pure methyl lactate to highly pure lactic acid was followed exactly as mentioned under Example-10. Highly pure lactic acid obtained here was clear and transparent and was analyzed by HPLC and showed highly pure lactic acid of 99.7% purity by wt. on water free basis. No trace of methanol and methyl lactate was observed in the L-(+)-Lactic Acid as analyzed by GC.

The main advantages of the present invention are:
1. The method of esterification reaction reported in this invention is continuous counter current trickle phase esterification of dilute crude lactic acid using methanol that gives 95 to 98.5% selectivity towards methyl lactate based on the lactic acid consumed.
2. The use of stabilizer reported in this invention, such as 4-methoxy phenol and hydroquinone reduces polymerization of lactic acid as well as oxidation of lactic acid to pyruvic acid or other bye products in the total reaction.
3. Also the use of above-mentioned stabilizer reported in this invention has reduced the side product formation from lactic acid, which in turn has given higher conversion of lactic acid to the methyl lactate.
4. The superheated methanol vapors fed in the reboiler bottom helps to remove water from lactic acid and water of reaction towards top of the column, where as the methyl lactate formed in the column trickles down in counter current fashion towards reboiler and thus arrests the reversible reaction which in turn helps to enhance the forward reaction of lactic acid to methyl lactate. The net effect of the above-mentioned operation is to get the higher conversion of lactic acid to methyl lactate is achieved.
5. The method reported in this invention permits molar ratio of methanol to lactic acid as low as 2.8.
6. The method reported in this invention easily permits recovery and recycle of the excess and un-reacted methanol back to the reaction zone.
7. The methyl lactate produced by this invention has the quality of 99.81% by wt purity on GC and has very low moisture content of 0.03% by wt and shows optical rotation of (−) 8.43. In spite of incorporating various impurities such as acetic acid, oxalic acid, fumaric acid and malic acid in feed crude dilute lactic acid, the product methyl lactate purity remained same.
8. In practicing the invention, any strong mineral acid may be used to generate lactic acid from calcium lactate, but sulfuric acid is preferred in view of the fact that this is readily available and inexpensive. It would be generally be used in the practice of a commercial embodiment of the invention for these reasons and it is described as illustrative.
9. The method of hydrolysis reaction reported in this invention of pure S-(−)-methyl lactate using highly pure water gives quantitative conversion and total selectivity towards L-(+)-lactic acid based on the methyl lactate consumed.
10. The use of reagent mixture reported in this invention, such as sodium bicarbonate and urea or sodium bicarbonate and thiourea mixture reduces the impurity of dimethyl ester of dicarboxylic acid present in methyl lactate. This treatment helps to get the highly pure L-(+)-lactic acid.
11. The use of highly pure L-(+)-lactic acid as the catalyst in the hydrolysis helps to accelerate the hydrolysis reaction and drives it to completion in short time. Similarly, it does not contaminate the L-(+)-lactic acid produced.
12. The use of pre-treated activated carbon helps to remove any coloring bodies in lactic acid. The pre-treatment of carbon removes any water and acid soluble impurities adhered to activated carbon.
13. The method reported in this invention permits molar ratio of methyl lactate to lactic acid as low as 4.8:1.0.
14. The method reported in this invention easily permits recovery and recycle of the methanol obtained from hydrolysis reaction back to the esterification zone.
15. The L-(+)-lactic acid produced by this invention has the quality of 99.81% by wt purity on HPLC on water free basis. Similarly the methyl lactate containing methyl esters of various impurities such as acetic acid, oxalic acid, fumaric acid and malic acid, pyruvic acid on treatment with reagents like sodium bicarbonate, mono ethanolamine or di-ethanolamine and urea gives highly pure S-(−)-methyl lactate, which on hydrolysis gives the product L-(+)-lactic acid of high purity.
16. The method reported in this invention can be viable commercially. The process reported in this invention is safe to operate and easy to control on large scale, thus it makes process commercially viable.

Thus in the methods of this invention, as compared to the usual methods, extremely high quality goods are obtained in high yields and highly pure S-(−)-methyl lactate and highly pure L-(+)-lactic acid can be produced.

In view of the many modifications possible in the process and in the apparatus, it will be understood that the above-described apparatus and typical method described above are illustrative and should not be regarded as limiting the scope of the following claims:

We claim:
1. A process for preparation of highly pure L-(+)-Lactic acid, the said process comprising the steps of:
   (a) esterifying crude dilute lactic acid solution in water using mineral acid by preheating the above said crude dilute lactic acid at a temperature of about 105° C. and allowing it to react with superheated methanol vapors maintained at about 150° C., wherein the molar ratio of methanol to lactic acid is 2.8:1 to 4:1, in the presence of stabilizer, in continuous counter current trickle phase mode to obtain the methyl lactate, removing continuously unreacted methanol and water rich layer separately as distillate and crude methyl lactate in a continuous manner as overflow from reactor bottoms followed by recovery of methyl lactate using evaporator with lactic acid to methyl lactate conversion of about 98.5% with no other by-product formation,
   (b) reacting the above pure methyl lactate having purity 93-95% wt. with a mixture of sodium bicarbonate and a reagent selected from the group consisting of urea or thiourea, monoethanlomine or di-ethanolamine or a mixture thereof, under reflux, for a period of 1 hr. to convert volatile impurities into non-volatile components, followed by distillation with or without vacuum to obtained desired highly pure S-(−)-methyl lactate having purity of 99.8% by wt, moisture of 0.03% and optical purity of (−) 8.43°,
   (c) hydrolyzing the above S-(−)methyl lactate obtained in step (b) with distilled, metal contamination free or de-mineralized or de-ionized water, in the presence of pure L(+)-lactic acid as catalyst with a molar ratio of S-(−)-methyl lactate to catalyst in the range of 10.8:1 to 3.4:1, at a temperature in the range of 85-105° C., for a period of 2-6 hrs. and allowing hydrolysation of S-(−)-methyl lactate to L-(+)lactic acid with the removal of methanol obtained during hydrolysis reaction continuously under reflux, at controlled temperature and pressure to obtain the pure L-(+)-lactic acid followed by treating with pre-treated activated carbon, wherein pre-treatment is carried out by washing activated carbon with a solution of pure lactic acid, to obtain the highly pure L-(+)-lactic acid solution in water and concentrating it in an evaporator to attain purity in the range of 99-99.8% and optical purity of 99-99.9% on water free basis and continuously collecting the methanol in a reservoir for being used/recycled in step (a).

2. A process for the preparation of lactic acid as claimed in claim 1 characterized in step (b) in converting volatile impurities of S-(−)-methyl lactate into non volatile components before hydrolysis by using a mixture of sodium bicarbonate with a reagent selected from the group consisting of urea, monoethanolamine, di-ethanolamine and a mixture thereof.

3. A process as claimed in claim 1 characterized in step (c) in using lactic acid of 99-99.8% purity as catalyst for accelerating the hydrolysis of S-(−)-methyl lactate.

4. A process as claimed in claim 1, characterized in step (a) in continuous counter current trickle phase esterification of heated lactic acid with super heated methanol in vapor phase in counter current mode and obtaining S-(−)-methyl lactate in a continuous mode.

5. A process as claimed in claim 1, characterized in step (a) in using stabilizer selected from 4-methoxy phenol and hydroquinone.

6. A process as claimed in claim 1, wherein the volatile impurity present in methyl lactate having purity of about 95% used in step (b) is mono or dicarboxylic acid ester selected from dimethyl oxalate, dimethyl fumarate, methyl acetate and a mixture thereof.

7. A process as claimed in claim 1, wherein the catalyst used in step (c) is pure lactic acid of about 90% by wt.

8. A process as claimed in claim 1, wherein the activated carbon used in step (c) is pretreated by washing it with about 10% aqueous solution of pure L-(−) lactic acid.

9. A process as claimed in claim 1 characterized in step (c), wherein the molar ratio of methyl lactate to catalyst, lactic acid, used is 4.8:1.0.

10. A process as claimed in claim 1, wherein the time period used in step (c) for complete hydrolysis of methyl lactate is preferably in the range of 4-6 hrs.

11. A process as claimed in claim 1, wherein the purity of lactic acid obtained in step (c) is about 99.8% by wt. on water free basis.

12. A process as claimed in claim 1, wherein the optical purity of lactic acid obtained in step (c) is 99.9%.

13. A process as claimed in claim 1, wherein the fresh or recycled methanol used for esterification of lactic acid in step (a) is a super heated methanol vapor.

14. A process as claimed in claim 1, wherein the use of stabilizer increased the lactic acid to methyl lactate conversion from 95% to 98.5% with no other bye product formation.

15. A process as claimed in claim 1, wherein the mole ratio of methanol to lactic acid is 2.8 to 1.

16. A process as claimed in claim 1, wherein the ratio of catalyst to lactic acid is in the range of 0.005:100 to 0.02:100 on a mole basis.

17. A process as claimed in claim 1, wherein the high purity of S-(−)-methyl lactate obtained is in the range of 99.50 to 99.85% by wt. with about 0.03% by wt. moisture.

18. A process claimed in claim 1 characterized in step (b) wherein the use of sodium bi-carbonate is made in the distillation of methyl lactate and is in the range of 1 to 5% by wt of methyl lactate, preferably 1% by wt of methyl lactate.

19. A process as claimed in claim 1, wherein the L-(+)-lactic acid produced is odor and color free.

20. A process as claimed in claim 1, wherein the ratio of catalyst to lactic acid is in the range of 0.01:100 on a mole basis.

* * * * *